United States Patent
Baumgartner

(10) Patent No.: US 7,655,615 B2
(45) Date of Patent: Feb. 2, 2010

(54) METHOD FOR PRODUCING A BONE MATERIAL ENRICHED WITH BONE GROWTH FACTORS

(75) Inventor: Ludwig Baumgartner, Nuremberg (DE)

(73) Assignee: Tutogen Medical GmbH, Neunkirchen am Brand (DE)

( * ) Notice: Subject to any disclaimer, the term of this patent is extended or adjusted under 35 U.S.C. 154(b) by 1601 days.

(21) Appl. No.: 10/168,294

(22) PCT Filed: Dec. 5, 2000

(86) PCT No.: PCT/EP00/12234

§ 371 (c)(1),
(2), (4) Date: Oct. 22, 2002

(87) PCT Pub. No.: WO01/45720

PCT Pub. Date: Jun. 28, 2001

(65) Prior Publication Data

US 2003/0113360 A1    Jun. 19, 2003

(30) Foreign Application Priority Data

Dec. 22, 1999 (DE) ................ 199 62 248

(51) Int. Cl.
*A61K 38/00* (2006.01)
*A61K 38/16* (2006.01)
*C07K 14/00* (2006.01)

(52) U.S. Cl. ............ 514/2; 530/350; 424/198.1; 623/17.16

(58) Field of Classification Search .............. None
See application file for complete search history.

(56) References Cited

U.S. PATENT DOCUMENTS

| 4,394,370 A * | 7/1983 | Jefferies ............ 606/76 |
| 4,563,489 A | 1/1986 | Urist ............ 524/21 |
| 4,975,527 A | 12/1990 | Koezuka et al. ............ 530/356 |
| 5,405,390 A | 4/1995 | O'Leary et al. ............ 623/16 |
| 5,458,653 A | 10/1995 | Davidson ............ 623/23 |
| 2002/0098222 A1 * | 7/2002 | Wironen et al. ............ 424/423 |
| 2005/0142164 A1 * | 6/2005 | Lindholm et al. ............ 424/426 |

FOREIGN PATENT DOCUMENTS

| EP | 0069260 | 1/1983 |
| EP | 0 069 260 B1 | 9/1985 |
| GB | 2 164 042 A | 3/1986 |
| WO | WO 96/39203 | 12/1996 |
| WO | WO 97/31661 | 9/1997 |
| WO | WO 98/40113 | 9/1998 |

OTHER PUBLICATIONS http://www.m-w.com/dictionary/suck (Dec. 06, 2005).*
Abstract—Minamide et al. "Experimental spinal fusion using sintered bovine bone coated with type I collagen and recombinant human bone morphogenetic protein-2" Spine 24/18 (1863-1872), Sep. 15, 1999.

* cited by examiner

*Primary Examiner*—Gary B Nickol
*Assistant Examiner*—Xiaozhen Xie
(74) *Attorney, Agent, or Firm*—Gifford, Krass, Sprinkle, Anderson & Citkowski, P.C.

(57) ABSTRACT

The aim of the invention is to produce a bone material which is enriched with bone growth factors and whose bone growth factors are released in a delayed manner after surgically applied in the body. To this end, the invention provides a method according to which the bone material is loaded with a bone growth factor or with a mixture of bone growth factors and is then coated with a reabsorbable substance.

3 Claims, No Drawings

METHOD FOR PRODUCING A BONE MATERIAL ENRICHED WITH BONE GROWTH FACTORS

So-called BMPs (bone morphogenetic proteins) play a decisive role in the growth of human or animal bones. Expedient methods have been developed to harvest these growth factors in which bone material was demineralized and growth factors were enriched in the demineralized bone material. The bone material enriched with growth factors is used in particular in surgery to promote bone growth at defective areas and to accelerate the healing process of the bone.

Methods are furthermore known of separating and harvesting different growth factors from bones. In deviation from this, preparative amounts of bone growth factors can be gained in a genetic engineering manner.

In previously practiced methods it is disadvantageous that, when bone material enriched with bone growth factors is used in surgery, the bone growth factors are prematurely washed out so that the accelerated bone growth cannot be maintained over the total healing process of the bone.

The underlying object of the invention is to provide a method with which a bone material enriched with bone growth factors can be manufactured with an improved release rate.

This object is satisfied in accordance with the invention by a method as detailed herein.

The invention is based on the recognition that the surface and/or the interior of bone material can also be sheathed by a resorbable material with the aid of a suitable method, with the sheathing of a bone material enriched or charged with bone growth factors then bringing about the intended delayed release of the bone growth factors. In this manner, in a surgical use of the bone material as a transplant, the bone growth factors can be released continuously over a longer period and over the total healing process of a bone, with the length and the speed of the release being dependent on the properties of the sheathing. A control of the agent release is possible, for example, via the thickness and the material composition of the sheathing.

Advantageous embodiments of the invention are described in the description and the dependent claims.

A solution or suspension of the bone growth factors is advantageously sprayed or trickled onto the surface of a suitable bone material, for example bovine spongiosa, which has been freed of bone marrow in a conventional manner. It is furthermore possible to immerse the bone material into the solution so that the solution is drawn in by the surface of the bone material. In this connection, the bone growth factors are predominantly, but not exclusively, deposited in a surface region of the bone material, with the bone material enriched with bone growth factors being sheathed subsequent to this treatment.

To enrich the bone growth factors increasingly also at the interior of the bone material, in a further development a vacuum is applied during the spraying on, trickling on or drawing in of the solution or suspension. Air, which otherwise prevents the entrance of solvent or suspension, is evacuated from the interior of the bone material by the vacuum applied.

In a further variant, the charged bone material, which is thus enriched with bone growth factors, is embedded in prefabricated capsules, hollows or pockets of resorbable material for sheathing.

In accordance with a further embodiment, the bone growth factors can be homogeneously distributed in a solution or suspension of the resorbable material. This solution or suspension can subsequently be sprayed or trickled onto the surface of the bone material. It is furthermore possible to immerse the bone material into the said solution or suspension. In the above-described process steps, the solution or suspension essentially only penetrates into the surface region of the bone material. The treatment of the bone material with bone growth factors, which takes place at the same time, and its sheathing with resorbable material, therefore substantially remains limited to the surface, with both the bone growth factors and the bone material being sheathed by the resorbable material in this manner.

In a preferred embodiment of the method in accordance with the invention, a vacuum is applied during the trickling on, spraying on or drawing in of the solution or suspension containing the resorbable solution or suspension so that the interior of the bone material is also increasingly enriched and sheathed with sheathed bone growth factors.

Collagen, which is available in a dissolved or dispersed manner or as a gel, is advantageously used as the resorbable material. Further examples of resorbable materials are gelatin or oxycellulose. The bone material can be used in the form of blocks, chips or powder. In accordance with the invention, it can be available in a usual mineral/matrix composition. Expediently, however, bone material is used in the method in accordance with the invention which is fully or partly demineralized. The bone material used can be both of animal and of human origin.

In a further advantageous variant, the bone growth factor(s) are homogeneously distributed in a solution or suspension of the resorbable material. Subsequently, bone material is introduced into this solution in the form of powder or chips and the intermediate product thus obtained dried, preferably freeze dried, to form a sponge-like body. A product which is extremely helpful for surgery can hereby be obtained.

In an expedient further development, the bone material is also charged with at least one anti-biotic. The charging can take place in any desired manner, for example by the addition of the antibiotic to the solution or suspension of the resorbable material or by trickling the antibiotic onto the bone material. The charged bone material sheathed with resorbable material is preferably freeze dried or dried by heat.

In a further expedient further development, the charged and sheathed bone material is produced in a germ-free manner or is sterilized after the drying.

Two examples of the method in accordance with the invention will be described in the following:

EXAMPLE 1

100 ml of an 0.5% collagen solution produced in a known manner are mixed with 100 mg rhBMH-2 in a vessel and carefully stirred until homogenous. A bovine spongiosa bone with the dimensions $3\times3\times2$ cm$^3$ is subsequently immersed into the collagen/BMP solution and left in the solution under vacuum for 10 minutes. The spongiosa block treated in this manner is subsequently removed from the vessel, put into a tub and frozen and dried in steps in a freeze drying unit. Finally, the spongiosa block enriched with BMP and sheathed with collagen is sterilized in a suitable manner.

The spongiosa block produced in accordance with the method described contains BMP enclosed in collagen so that a premature washing out in a surgical application as a transplant is prevented. A delayed release of BMP takes place in accordance with the collagen depletion.

An accelerated new formation of bone at a defective area takes place due to the inductive effect of the BMPs enriched in the transplant.

EXAMPLE 2

100 ml of a 1.0% collagen solution produced in a known manner are mixed with 100 mg rhBMP-2 in a vessel and carefully stirred until homogeneous. The BMP/collagen solution is subsequently poured into a metal tub and bone material is added, for example in the form of chips of bovine bone of a diameter of approximately 8 millimeters and a vacuum is applied for the better penetration of the chips with solution. The tub with contents is frozen and dried in steps in a freeze drying plant. Finally, the resulting product is sterilized in a suitable manner.

The invention claimed is:

1. A method of manufacturing a bone material enriched with bone growth factors, comprising charging a surface and/or an interior of the bone material with at least one bone growth factor (BMP) and wherein the bone material is initially charged by spraying on, trickling on or drawing in of a solution or suspension of the at least one bone growth factor or by immersing into a solution or suspension of the bone growth factor; and sheathing thereafter the bone material with a resorbable material to yield the enriched bone material, characterized in that the bone material is charged with at least one antibiotic.

2. A method of surgical transplant characterized in transplanting an enriched bone material into a subject, the enriched bone material being manufactured from a bone material by a method comprising:

charging a surface and/or an interior of the bone material with at least one bone growth factor (BMP) and wherein the bone material is initially charged by spraying on, trickling on or drawing in of a solution or suspension of the at least one bone growth factor or, by immersing the bone material into a solution or suspension of the bone growth factor; and sheathing thereafter the bone material with a resorbable material to yield the enriched bone material.

3. A method in of manufacturing a bone material enriched with bone growth factors, comprising charging a surface and/or an interior of the bone material with at least one bone growth factor (BMP) and wherein the bone material is initially charged by spraying on, trickling on or drawing in of a solution or suspension of the at least one bone growth factor or by immersing into a solution or suspension of the bone growth factor; and sheathing thereafter the bone material with a resorbable material to yield the enriched bone material, characterized in that the resorbable material is selected from the group consisting of gelatin, polyglycol acid, polylactic acid, oxycellulose, fibrin adhesive, and acrylic adhesive.

* * * * *

UNITED STATES PATENT AND TRADEMARK OFFICE
CERTIFICATE OF CORRECTION

PATENT NO.       : 7,655,615 B2             Page 1 of 1
APPLICATION NO.  : 10/168294
DATED            : February 2, 2010
INVENTOR(S)      : Ludwig Baumgartner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2119 days.

Signed and Sealed this

Twenty-third Day of November, 2010

David J. Kappos
*Director of the United States Patent and Trademark Office*